United States Patent [19]

Strickler et al.

[11] Patent Number: 5,359,105
[45] Date of Patent: Oct. 25, 1994

[54] DEPROTONATION OF CYCLOPENTADIENYL DERIVATIVES

[75] Inventors: Jamie R. Strickler; John M. Power, both of Baton Rouge, La.

[73] Assignee: Albemarle Corporation, Richmond, Va.

[21] Appl. No.: 144,463

[22] Filed: Nov. 1, 1993

[51] Int. Cl.$^5$ ............ C07F 7/08; C07F 7/10; C07F 7/18; C07F 3/02

[52] U.S. Cl. ............ 556/410; 556/19; 556/22; 556/26; 556/87; 556/96; 556/404; 556/405; 260/665 R

[58] Field of Search ............ 556/410, 87, 96, 19, 556/22, 26, 404, 405; 260/665 R

[56] References Cited

U.S. PATENT DOCUMENTS

| | | | |
|---|---|---|---|
| 2,667,501 | 1/1954 | Martin | 556/410 |
| 4,383,119 | 5/1983 | Pullukat et al. | 556/410 X |
| 4,447,369 | 5/1984 | Ashby | 260/665 R |
| 5,017,717 | 5/1991 | Wright et al. | 556/410 X |
| 5,026,887 | 6/1991 | Kobayashi et al. | 556/410 X |
| 5,081,091 | 1/1992 | Ballard et al. | 556/410 X |
| 5,141,676 | 8/1992 | Bogdanovic et al. | 260/665 R |
| 5,231,205 | 7/1993 | Rieke | 260/665 R |

FOREIGN PATENT DOCUMENTS

| | | | |
|---|---|---|---|
| 0416815 | 3/1991 | European Pat. Off. | C08F 10/00 |
| 9308199 | 4/1993 | World Int. Prop. O. | C07F 7/28 |
| 9308221 | 4/1993 | World Int. Prop. O. | C08F 10/00 |

*Primary Examiner*—Paul F. Shaver
*Attorney, Agent, or Firm*—David M. Bunnell

[57] ABSTRACT

Cyclopentadienyl derivatives are deprotonated by a process whereby the cyclopentadienyl derivatives are reacted with a Grignard reagent in an inert solvent which contains from about 0.5 to 1.5 equivalents per equivalent of cyclopentadienyl derivative of a cyclic ether or an acyclic polyether, so as to form a dianionic salt of said cyclopentadienyl derivative.

9 Claims, No Drawings

DEPROTONATION OF CYCLOPENTADIENYL DERIVATIVES

The invention relates generally to the preparation of salts of cyclopentadienyl derivatives which are useful intermediates in the preparation of metallocenes and more specifically to an improved process for the deprotonation of cyclopentadienyl derivatives using a Grignard reagent.

Metallocenes are useful components of olefin polymerization systems. The metallocenes include a cyclopentadienyl ligand which is complexed with a transition metal salt. Before coordinating the ligand to the transition metal salt, the ligand must be deprotonated using a Grignard reagent to form dianionic salt of the ligand. In one such process, a ligand is added to a solution of a Grignard reagent in a 4:1 by volume toluene/THF mixture. The THF is present in about a ~10 times molar excess to the amount of ligand and the reaction requires 1 to 2 days. At shorter times, the product contains relatively large amounts of the monoanion salt.

We have now discovered a deprotonation process which can provide dianionic salts in high yields and purity in reduced reaction times.

In accordance with this invention there is provided a process for the deprotonation of a cyclopentadienyl derivative. The process comprises reacting a Grignard reagent with the cyclopentadienyl derivative in an inert solvent which contains from about 0.5 to 1.5 equivalents, per equivalent of the cyclopentadienyl derivative, of a cyclic ether or a acyclic polyether so as to form a dianionic magnesium halide salt of the cyclopentadienyl derivative.

Cyclopentadienyl derivatives which can be deprotonated by the process of this invention include those having a single cyclopentadienyl group or two cyclopentadienyl groups connected by a bridging group such as an alkylene or a silanylene group. The cyclopentadiene ring can be substituted, for example, with alkylene, cyclic alkylene, germanyl and/or silyl groups. Such ligands are known in the art. One type of ligand to which the process is especially applicable has the formula Cp'YZH wherein Cp' is a cyclopentadienyl or a substituted cyclopentadienyl group, Y is a covalent bridging group which contains one or more Group 14 elements (new IUPAC notation, Group IVA of the old notation) and, preferably, silicon, germanium and/or carbon, and ZH is a heteroatom ligand of an element having a coordination number of 2 or 3 and, preferably, oxygen, nitrogen, phosphorus or sulfur which may include a radical selected from C1–C20 hydrocarbyl radicals and substituted C1 to C20 hydrocarbyl radicals.

Preferred cyclopentadienyl groups Cp' can be represented by the formula:

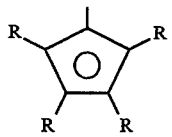

wherein R each occurrence is hydrogen or a moiety selected from the group consisting of silyl, germyl, hydrocarbyl, substituted hydrocarbyl and combinations thereof having up to 20 (preferably 1 to 10) carbon, germanium and/or silicon atoms, and two R substituents can together form a ring fused to the cyclopentadienyl moiety. Non-limiting examples of fused ring cyclopentadienyl derivatives include indenyl, tetrahydroindenyl, fluorenyl, octahydrofluorenyl, and the like, which rings can be further substituted. Non-limiting examples of other suitable R groups, which R groups can be the same or different and can be substituted for 1 to 4 hydrogen atoms on the cyclopentadienyl ring, include straight or branched chain hydrocarbyl radicals, including halogen and alkoxy substituted hydrocarbyl radicals, cyclic hydrocarbyl radicals, including alkyl, alkoxy and halogen, substituted cyclic hydrocarbyl radicals, aromatic hydrocarbyl radicals including alkyl, alkoxy and halogen substituted aromatic radicals, and organometalloid radicals of silicon and germanium. Specific non-limiting examples of preferred R moieties include methyl, ethyl, propyl, butyl, pentyl, hexyl, (including isomers), norbornyl, benzyl, phenyl, trimethylsilyl, triethylsilyl, ethyldimethylsilyl, methyldiethylsilyl, phenyldimethylsilyl, methyldiphenylsilyl, triphenylsilyl, triphenylgermyl, trimethylgermyl, methylmethoxy, methylethoxy, and the like.

Preferred bridging groups, Y, contain 1–4 atoms in the bridge, which atoms are selected from Group 14 elements of the Periodic Table and especially silicon, germanium and carbon. Non-limiting examples of bridging groups are $SiR_2'$, $CR_2'$, $SiR_2'SiR_2'$, $CR_2'CR_2'$, $CR_2'SiCR_2'$, $CR'=CR'$, $GeR_2'$ wherein R' each occurrence is hydrogen or a moiety selected from silyl, germanyl, hydrocarbyl, substituted hydrocarbyl (e.g. aralkyl, alkaryl, haloalkaryl and haloaralkyl) and combinations thereof having up to 20 non-hydrogen atoms. Specific non-limiting examples of preferred R' moieties include methyl, ethyl, propyl, butyl, pentyl, hexyl (including isomers), trimethylsilyl, triethylsilyl, ethyldimethylsilyl, methyldiethylsilyl, phenyldimethylsilyl, methyldiphenylsilyl, triphenylsilyl, triphenylgermyl and the like. The halogen on the bridging group can be chlorine, bromine or iodine and, preferably, is chlorine.

Preferred heteroatom ligands ZH can be represented by the formula $AR''_{(x-2)}H$ in which A is an element with a coordination number (x) of three from Group 15 or an element with a coordination number of two from Group 16 of the Periodic Table of Elements, (new IUPAC notation, Groups V A and VI A of the old notation) preferably nitrogen, phosphorus, oxygen or sulfur, and R" is a radical selected from the group consisting of $C_1$–$C_{20}$ hydrocarbyl radicals wherein one or more hydrogen atoms are replaced by a halogen radical, an amino radical, a phosphino radical, an alkoxy radical or any other radical containing a Lewis acidic or basic functionality and is the coordination number of the element A. Specific non-limiting examples of heteroatom ligands include, t-butylamino, phenylamino, p-n-butylphenylamino, cyclohexylamino, perfluorophenylamino, n-butylamino, methylamino, ethylamino, n-propylamino, benzylamino, t-butylphosphino, ethylphosphino, phenylphosphino, cyclohexylphosphino, hydroxyl and sulfino.

Preferred Grignard reagents have the formula R'''MgX, where R''' is $C_1$ to $C_{10}$ hydrocarbyl and X is halogen. More preferred are $C_3$ or $C_4$ alkyl magnesium chlorides and bromides such as isopropyl magnesium chloride, isopropyl magnesium bromide, n-butylmagnesium bromide, isobutylmagnesium chloride and the like. The Grignard reagents are used in about a stoichiometric amount or about 2 moles of reagent to one mole of ligand. Preferably a slight (5 to 10%) excess of the Grignard reagent is used because it is the less expensive reactant.

Suitable ether solvents are cyclic ethers and acyclic polyethers having from about 4 to 10 carbon atoms. Non-limiting examples of such ethers include tetrahydrofuran (THF), ethylene glycol dimethyl ether (DME or glyme), 1,4-dioxane, 2-methoxyethyl ether (diglyme), triethylene glycol dimethyl ether, tetrahydropyran, diethylene glycol dimethyl ether, and the like. The preferred ether is THF. Suitable amounts of ether are from about 0.5 to 1.5 equivalents per equivalent of ligand, preferably, from about 0.5 to 1.0 equivalent per equivalent of ligand and more preferably from about 0.5 to less than 1.0 equivalent per equivalent of ligand. About 0.5 equivalents is sufficient to avoid gel formation. The use of an excess of ether results in the presence of mono-MgCl salt and other impurities in the product and reduces the yield of the desired di-salt. This indicates that excess ether slows the reaction such that reaction times of two days are needed to get a high yield of dianionic salt product.

The reaction is carried out in an inert solvent and, preferably, an aromatic hydrocarbon solvent such as benzene, toluene or xylenes. From about 10 to 30% w/v solutions of ligand in solvent are preferred.

According to a preferred mode of conducting the process, the ligand solution is mixed with the ether in a stirred reactor and heated to reaction temperature. The Grignard reagent is then added slowly to the reaction mixture. Reaction temperatures preferably range from about 75° to 100° C. After the addition of the Grignard reagent has been completed, the mixture is stirred and heated until the reaction is completed. Typical reaction times range from 4 to 22 hours. Good yields can be obtained in six hours or less.

Some product will precipitate from the reaction mixture during the process, but the mixture does not gel and remains fluid. When the reaction has been completed and the reaction mixture cooled to ambient temperature, additional product can be precipitated by adding an aliphatic hydrocarbon solvent such as pentane, hexane or Isopar C. The product can then be collected by filtration.

The process of the invention is further illustrated by, but is not intended to be limited to, the following examples.

EXAMPLE 1

$(MgCl)_2[(C_5Me_4)SiMe_2N-t-Bu]$.THF Prepared with 0.56 Equivalents of THF Present $(C_5Me_4H)SiMe_2(NH-t-Bu)$ (11.62 g. 46.2 mmol) was diluted to approximately 10% w/v with toluene in a 500 mL Schlenk flask. THF was also added to this solution (25.9 mmol). The flask was adapted with an addition funnel and Friedrichs condenser. This solution was stirred with a magnetic stir bar and heated to approximately 85° C. in an oil bath. At this temperature, i-PrMgCl (2.0M in Et$_2$O; 48 mL, 96 mmol) was added dropwise over 27 minutes. Propane was evolved from the reaction during the addition. Off-white solids formed towards the end of the addition. The slurry stirred easily. Some solids adhered to the flask. The solution was heated between 99 and 107° C. overnight (22 hours). The slurry was cooled to ambient temperature and was then taken into the drybox. Approximately one equivalent of THF was added (3.0 g, 42 mmol). Hexanes were added (105 mL) forcing more precipitate to form. The slurry was again stirred overnight. The solids were filtered on a 150 mL coarse frit, washed with hexanes (75 mL) and dried in vacuo. The solids were fine and white. The yield was 18.21 g (41.2 mmol, 89%). 1H NMR in thf-d8 showed 98% product and only 2% of the monoanion, $(MgCl)[(C_5Me_4)SiMe_2(NH-t-Bu].2THF$.

EXAMPLE 2

$(MgCl)_2[(C_5Me_4)SiMe_2N-t-Bu]$.THF Prepared with 1.0 Equivalents of THF Present $(C_5Me_4H)SiMe_2(NH-t-Bu)$ (11.16 g, 44.4 mmol) was diluted to approximately 10% w/v with toluene in a 500 mL Schlenk flask. THF was added to this solution (44.4 mmol). The flask was adapted with an addition funnel and Friedrichs condenser. This solution was stirred with a magnetic stir bar and heated to approximately 85° C. in an oil bath. At this temperature, i-PrMgCl (2.0M in Et$_2$O; 46 ml, 92 mmol) was added dropwise over one hour. Propane was evolved from the reaction during the addition. Off-white solids formed towards the end of the addition. The solution was heated between 98 and 109° C. overnight (20 hours). The slurry stirred easily. The slurry was cooled to ambient temperature and was then taken into the drybox. Hexanes were added (100 mL) forcing more precipitate to form. The slurry was again stirred overnight. The solids were filtered on a 150 mL coarse frit, washed with hexanes (2×25 mL), and dried in vacuo. The solids were fine and almost white. The yield was 17.66 g (40.0 mmol; 90%). $^1$H NMR in thf-d8 showed 96% product and 4% of the monoanion, $(MgCl)[(C_5Me_4)SiMe_2(NH-i-Bu].2THF$.

EXAMPLE 3

$(MgCl)_2[(C_5Me_4)SiMe_2N-t-Bu]$.THF Prepared with 1.5 Equivalents of THF Present $(C_5Me_4H)SiMe_2(NH-t-Bu)$ (10.02 g, 39.8 mmol), THF (4.31 g, 59.8 mmol), and 100 mL of toluene were combined in a 500 mL Schlenk flask. The flask was adapted with an addition funnel and Friedrichs condenser. This solution was stirred with a magnetic stir bar and heated to approximately 85° C. in an oil bath. Isopropylmagnesium chloride (2.0M in Et$_2$O; 41 mL, 82 mmol) was then added dropwise over 22 minutes. Propane was evolved from the reaction during the addition. The solution was heated between 108° and 117° C. overnight (22 hours). The slurry stirred easily. The slurry was cooled to ambient temperature. Hexanes were added (100 mL). The slurry was again stirred overnight. The white solids were filtered on a 150 mL coarse frit, washed with hexanes (30 mL), and dried in vacuo. The yield was 15.45 g (35.0 mmol; 88%). $^1$H NMR in thf-d8 showed 91% product and 9% of the monoanion, $(MgCl)[(C_5Me_4)SiMe_2(NH-t-Bu].2THF$.

Examples 1-3 show that, at comparable reaction times, as the amount of THF was increased, then the amount of monoanion impurity also increased.

EXAMPLE 4

$(MgCl)_2[(C_5Me_4)SiMe_2N-t-Bu]$.THF Prepared with 0.65 Equivalents of THF Present—6 Hour Reaction $(C_5Me_4H)SiMe_2(NH-t-Bu)$(14.99 g, 59.6 mmol) was diluted to approximately 10% w/v with toluene in a 500 mL Schlenk flask. THF was also added to this solution (2.65 g, 36.6 mmol). The flask was adapted with an addition funnel and Friedrichs condenser. This solution was stirred with a magnetic stir bar and heated to approximately 85° C. in an oil bath. At this temperature, i-PrMgCl (2.0M in Et$_2$O; 67 mL, 134 mmol) was added dropwise over 30 minutes. Propane was evolved from the reaction during the addition. Off-white solids formed towards the end of the addition. The slurry stirred easily. The solution was heated between 108° and 110° C. for 6 hours. The slurry was allowed to cool slightly and then 8.50 g (120 mmol) of THF were added. Heptane was added (150 mL) forcing more precipitate to form. The slurry was stirred overnight. The solids were filtered on a 150 mL coarse frit, washed with hexanes (50 mL), and dried in vacuo. The solids were fine and white. The yield was 25.25 g (57.2 mmol, 96%). $^1$H NMR in thf-d8 showed 94% product and 6% of the monoanion, (MgCl)[(C$_5$Me$_4$)SiMe$_2$(NH-t-Bu].2THF.

Comparison 1

Isolation of (MgCl)$_2$[(C$_2$Me$_4$)SiMe$_2$N-t-Bu].THF Using THF As a Post-Treatment (C$_5$Me$_4$H)SiMe$_2$(NH-t-Bu) (30.02 g, 0.119 mol) was diluted to approximately a 10% w/v with 300 mL of toluene in a 1-L, 5-neck flask. The flask was adapted with a mechanical stirrer, addition funnel and Friederichs condenser. The solution was heated to approximately 85° C. in an oil bath and then i-PrMgCl (2.0M in Et$_2$O; 127 mL, 0.254 mol) was added dropwise over 45 minutes. Propane was evolved from the reaction during the addition. The solution was heated between 95° and 100° C. for 22 hours. The flask filled with gelatinous solids overnight. Even at higher stir rates, some difficulty with stirring was encountered during the latter part of the reaction. The reaction was cooled to 78° C. and 3 equivalents of THF were added (29 mL, 0.356 mol). The gel dissolved and within a minute, an easily stirred solid formed. After heating for 35 minutes, the reaction was cooled to ambient temperature and hexanes were added (300 mL). More solids precipitated. After stirring overnight the solids were filtered on a 350 mL coarse frit, washed with hexanes (75 mL), and dried in vacuo. The yield was 45.53 g (0.103 mol; 91%). $^1$H NMR in thf-d8 showed 96% product and 4% (MgCl)[(C$_5$Me$_4$)SiMe$_2$(NH-t-Bu].2THF. This demonstrates that the absence of THF at the start of the reaction resulted in gel formation.

Comparison 2

The reaction of (C$_5$Me$_4$)SiMe$_2$(NH-t-Bu].THF with i-PrMgCl in THF (C$_5$Me$_4$H)SiMe$_2$(NH-t-Bu) (10.00 g, 39.8 mol) was diluted with 100 mL of toluene in a 500 mL Schlenk flask. Isopropylmagnesium chloride (2.0M in THF; 41 mL, 82 mmol) was added all at once. The solution was stirred with a magnetic stir bar. The flask was adapted with a condenser and then the reaction was heated gradually to reflux. The clear, dark amber solution was heated between 103° and 110° C. for 20 hours . No solids formed. The dark amber solution was cooled to ambient temperature. Heptane was added (100 mL). The solution separated into two layers. Another 50 mL of heptane was added. A dark lower layer and a light yellow upper layer was still present. After stirring for an hour, some sticky solids have formed. After stirring overnight the oil had solidified on the walls of the flask. The solids were scraped and filtered on a 250 mL coarse frit. The solids were washed with heptane (50 mL) and dried in vacuo. The yield was 15.53 g. $^1$H NMR in thf-d8 showed 83% of dianion product and 17% of the monoanion, (MgCl)[(C$_5$Me$_4$)SiMe$_2$(NH-t-Bu].2THF. This demonstrates that a large excess of THF (~10 to 1) results in a large amount of monoanion impurity in the product and requires a more complicated work-up to recover the product.

As illustrated by the examples, the process of the invention can produce yields of about 90% deprotonated product, 95% or more of which is the desirable dianionic product, in reaction times of about 6 hours.

The presence of THF (even 0.5 equivalents) prevents gel formation by converting the deprotonated ligand to a crystalline THF solvate. The presence of more than equivalent amounts of THF slows the reaction and results in larger amounts of monoanion in the product and causes some decomposition. Thus, the advantages of the process of the invention include easier workup procedures, low viscosity, and better purity at shorter reaction times.

What is claimed is:

1. A process for the deprotonation of a cyclopentadienyl derivative, said process comprising reacting a Grignard reagent with said cyclopentadienyl derivative in an inert solvent which contains from about 0.5 to 1.5 equivalents per equivalent of said cyclopentadiene derivative of an ether selected from the group consisting of cyclic ethers and acyclic polyethers so as to form a dianionic magnesium halide salt of said cyclopentadiene derivative.

2. The process of claim 1 wherein from about 0.5 to 1.0 equivalent per equivalent of said cyclopentadiene derivative of said ether is present and said ether is tetrahydrofuran.

3. The process of claim 1 wherein said cyclopentadienyl derivative has the formula Cp'YZH wherein Cp' is a cyclopentadienyl or a substituted cyclopentadienyl group, Y is a covalent bridging group which contains one or more Group 14 elements, and ZH is a heteroatom ligand of a Group 16 element having a coordination number of 2 or a Group 15 element having a coordination number of 3.

4. The process of claim 3 wherein from about 0.5 to 1.0 equivalent per equivalent of said cyclopentadiene derivative of said ether is present and said ether is tetrahydrofuran.

5. The process of claim 1 wherein said Grignard reagent is added to a solution of said cyclopentadiene derivative in an inert solvent which contains said ether.

6. The process of claim 1 wherein from about 0.5 to 1.0 equivalent of ether per equivalent of cyclopentadiene derivative is present.

7. The process of claim 5 wherein from about 0.5 to less than 1.0 equivalent of ether per equivalent of cyclopentadiene derivative is present.

8. The process of claim 5 wherein said ether is tetrahydrofuran, said cyclopentadiene derivative is (C$_5$Me$_4$H)SiMe$_2$(NH-t-Bu) and said dianionic salt of said cyclopentadienyl derivative is (MgX)$_2$[(C$_5$Me$_4$)-SiMe$_2$(N-t-Bu].THF where X is halogen.

9. The process of claim 3 wherein ZH is a heteroatom ligand of one or more elements selected from the group consisting of oxygen, nitrogen, phosphorus and sulfur.

* * * * *